| United States Patent [19] | [11] Patent Number: 4,633,010 |
| Singh et al. | [45] Date of Patent: Dec. 30, 1986 |

[54] TERTIARY ARALKYL TRIURETHANE

[75] Inventors: Balwant Singh; Peter S. Forgione, both of Stamford, Conn.

[73] Assignee: American Cyanamid Company, Stamford, Conn.

[21] Appl. No.: 453,681

[22] Filed: Dec. 27, 1982

[51] Int. Cl.[4] ............... C07C 125/077; C07C 119/048
[52] U.S. Cl. ..................................... 560/25; 560/355
[58] Field of Search .................. 260/453 AR, 453 P; 560/25

[56] References Cited

U.S. PATENT DOCUMENTS

| 3,290,350 | 12/1966 | Hoover | 260/453 P |
| 3,644,536 | 2/1972 | Bafford | 260/618 R |
| 3,919,278 | 11/1975 | Rosenthal et al. | 260/453 P |
| 4,276,228 | 6/1981 | Nishino et al. | 260/453 AL |
| 4,338,256 | 7/1982 | Fujinami et al. | 260/453 A |
| 4,361,518 | 11/1982 | Singh et al. | 260/453 P |
| 4,399,074 | 8/1983 | Schaefer | 260/453 P |

Primary Examiner—Dolph H. Torrence
Attorney, Agent, or Firm—Steven J. Hultquist; Henry C. Jeanette; Michael J. Kelly

[57] ABSTRACT

1,3,5-Tris(1-isocyanatomethylethyl)benzene is disclosed as a component in coating formulations and the like.

1 Claim, No Drawings

TERTIARY ARALKYL TRIURETHANE

This invention relates to a novel tertiary aralkyl triisocyanate which is particularly useful in formulation of systems for producing light stable polyurethane coatings.

Triisocyanates have been found useful in a number of applications, for example, as components in polyurethane coating formulations, and RIM applications, as cross-linking agents, etc. The aliphatic isocyanates are particularly desirable in that products derived from them are known to be light stable. The commonly available aliphatic isocyanates, however, have low molecular weights and consequent high vapor pressures. Characteristically they are toxic and hazardous to handle. Aliphatic triisocyanates have been developed which are more suitable for commercial applications by reacting low molecular weight polyisocyanates to form higher molecular weight polyisocyanates which as a result have lower vapor pressure and are consequently safer to handle. One example is the reaction of hexamethylene diisocyanate with water to form the biuret derivative. Such compounds have disadvantages, such as the presence of unreacted isocyanate monomer and short shelf life, and typically have relatively low isocyanate content.

It is an important object of this invention to provide a polyisocyanate having the light stability imparting properties of the aliphatic isocyanates, but which is characterized by the low vapor pressure and consequent low toxicity of high molecular weight compounds by the introduction of an aromatic moiety while at the same time retaining a high NCO content.

It is also an important object of this invention to provide such a polyisocyanate which is inexpensive to manufacture, which is storage stable and which is readily blended in formulating polyurethane coating systems.

The polyisocyanate of this invention is 1,3,5-tris(1-isocyanato-1-methylethyl)benzene represented by the formula:

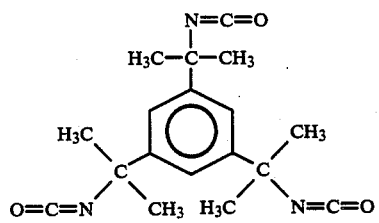

[I]

Surprisingly, despite the known stability of tertiary alkyl isocyanates the triisocyanate of this invention is highly reactive and is useful in providing polyurethane coating formulations which can be cured, tack-free, at room temperature.

1,3,5-tris(1-isocyanato-1-methylethyl)benzene is readily prepared from triisopropyl benzene which is available in quantity as a byproduct in cumene manufacture. A variety of processes for manufacture of the triisocyanate from triisopropyl benzene are available. These include either chlorination of the triisopropyl benzene to form tris α-chloroisopropyl benzene or dehydrogenation to the olefin, triisopropenylbenzene, either of which can be converted by reaction with isocyanic acid to 1,3,5-tris(1-isocyanato-methylethyl)benzene. Alternatively, the olefin can be reacted with a carbamic acid ester to form a tertiary aralkyl urethane which then can be cracked to the triisocyanate. The chloro compound product can also be reacted with sodium isocyanate to form the triisocyanate. It is also possible to form the triisocyanate of this invention by converting triisopropyl benzene to the corresponding triol which then can be reacted with a carbamic acid ester to form the corresponding tertiary aralkyl urethane and obtain the triisocyanate by cracking the urethane.

These reactions are as follows:

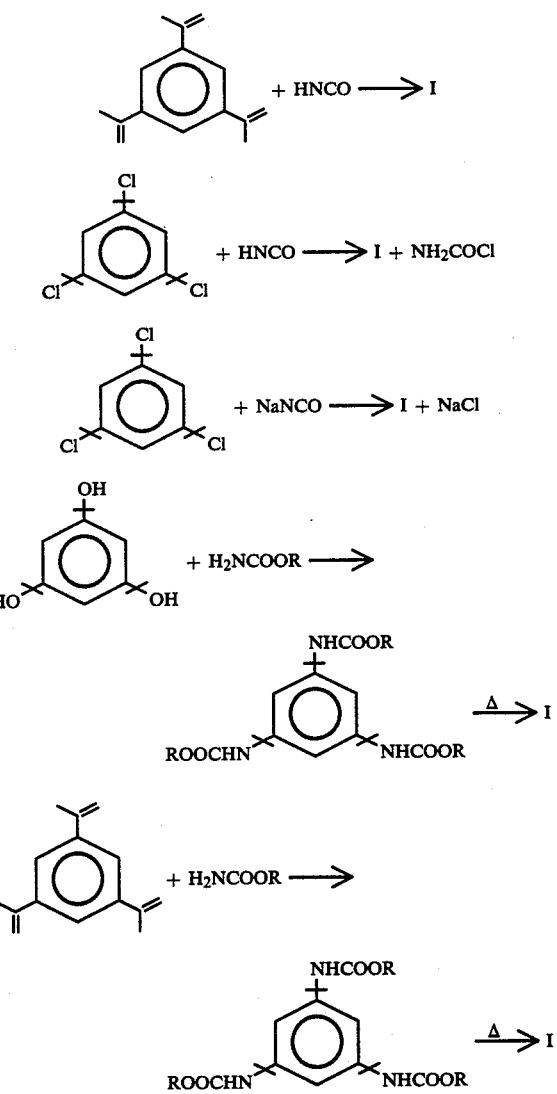

EXAMPLE 1

1,3,5-Tris(1-Isocyanato-1-Methylethyl)Benzene

A catalyst solution was prepared by stirring a mixture of zinc chloride (1.0 moles), pyridine (2.0 mole) and methylene dichloride until the solid dissolved. 1.42 moles of 90% sodium cyanate containing 0.5% $H_2O$ were added to 100 ml. of the solution so prepared which contained the equivalent of 24 m. moles of $Zn(pyr)_2Cl_2$. The mixture was stirred for an hour, and thereafter 0.33 moles of 1,3,5-tris(1-chloro-1-methylethyl)benzene dissolved in 530 ml. methylene chloride was added.

After stirring overnight at room temperature gas chromatographic analysis indicated 81% conversion to triisocyanate had been achieved. The solvent was evaporated, and the product was recrystallized from hexane giving a 59% yield; M.P. 65.5°–66.5° C.

The product was recrystallized in hexane solution, and dried, yielding a colorless solid having a melting point of 71°–72° C. Purity by gas chromatograph was 98.2 area percent 1,3,5-tris(isocyanatemethylethyl)benzene, 0.5 area percent of the diisocyanate and 0.5 area percent of the monoisocyanate. The NCO content was determined as 9.02 meg/g. which was 98.4 percent of theory. The product further contained 71 PPM zinc and 151 PPM total chloride.

The product was found to be very soluble in toluene, chloroform and methylene chloride, slightly soluble in hexane, and reactive with water and methanol.

The elemental analysis, calculated as $C_{18}H_{21}N_3O_3$, was:

|  | Carbon | Hydrogen | Nitrogen |
| --- | --- | --- | --- |
| Calculated | 66.03 | 6.47 | 12.83 |
| Found | 65.67 | 6.70 | 12.58 |

Structure was confirmed by NMR spectrum and infrared absorption spectral analysis as follows:

NMR δ—Value (CDCl$_3$) (60-MH$_z$) 7.28 (S, 3H, arom) and 1.73S (18H aliph.).

IR Spectrum, cm$^{-1}$ 2980, 2250, 1600, 1230, 1160, 920, 885, 785, and 710.

EXAMPLES II–IV

Comparable formulations of a proprietary polyester resin (MULTRON-221-75) with 1,3,5-tris(1-isocyanato-1methylethyl)benzene (TPTI), Desmodur-N, a proprietary triisocyanate which is the biuret derivative of hexamethylene diisocyanate, and T-1890, a proprietary triisocyanate which is the trimer of isophorone isocyanate, were prepared using an isocyanate to hydroxyl ratio of 1.1/1.0 on an equivalent weight basis. 1% of UL-28, a proprietary catalyst which is dimethyl tin dilaurate, was used with the TPTI formulation; 0.03% of UL-28 was used with the T-1890 formulation; and 0.015% UL-28 plus 0.015% lead napthenate was used with the Desmodur-N formulation.

Draw downs were made on 1200S aluminum using a No. 40 wirecator. The coatings were then cured at various temperatures, as indicated, and tested for hardness and solvent resistance, as indicated below.

| Example | II | III | IV |
| --- | --- | --- | --- |
| Isocyanate | TPTI | T-1890 | Desmodur-N |
| Cured at 125° C. - 20 minutes | | | |
| Thickness | 0.95 | 0.95 | 0.95 |
| Knoop hardness | 16.8 | 18.6 | 7.8 |
| MEK, MAR, rubs | — | — | — |
| MEK, remove, rubs | 200+ | 200+ | 200+ |
| Cured at 100° C. - 20 minutes | | | |
| Thickness | 0.95 | — | — |
| Knoop hardness | 15.6 | — | — |
| MEK, MAR, rubs | 70 | — | — |
| MEK, remove, rubs | 115 | — | — |
| Cured at 80° C. - 20 minutes | | | |
| Thickness | 0.95 | 0.95 | 0.9 |
| Knoop hardness | 11.5 | 17.4 | 1.8 |
| MEK, MAR, rubs | 20 | 5 | — |
| MEK, remove, rubs | 40 | 20 | 200+ |

EXAMPLE V

A suitable coating formulation using a proprietary 60% solids acrylic resin, G-cure 867, was made with an NCO/OH ratio of 1.1/1.0 using TPTI at 50% solids in toluene and 1% of UL 28. Draw downs were made on 1200S aluminum sheets using a No. 46 wirecator and were cured 20 minutes at 80°, 100° and 125° C. with the following results:

| Cure, T °C. | 80° | 100° | 125° |
| --- | --- | --- | --- |
| Thickness | 1.0 | 1.0 | 1.0 |
| Knoop hardness | 14.0 | 17.5 | 17.5 |
| MEK, MAR, rubs | 150 | — | — |
| MEK, remove, rubs | 200+ | 200+ | 200+ |

EXAMPLES VI–VII

Comparable formulations were prepared using a proprietary, moisture curable resin Acryloid AU-568, with TPTI (Example VI) and T-1890 (Example VII) at an NCO/OH ratio of 1.1/1.0 and without addition of catalyst. AU-568 resin possesses an oxazolidine functionality which acts as a site for cross-linking with isocyanate. This is inactive until activated with moisture to form an amine active hydrogen with which added isocyanate reacts rapidly and preferentially.

Draw downs were made on 1200S aluminum sheets using a No. 40 wirecator and cured 20 minutes at 80° and 100° C. with the following results:

| Example No. | TPTI VI | | T-1890 VII | |
| --- | --- | --- | --- | --- |
| Cure, T °C. | 80° | 100° | 80° | 100° |
| Thickness | tacky | 1.5 | tacky | 1.4 |
| MEK, remove, rubs | — | 50 | — | 60 |

EXAMPLES VIII and IX

Samples as prepared in Examples VI and VII were also cured at room temperature and evaluated after 4 days as follows:

| Example No. | TPTI VIII | T-1890 IX |
| --- | --- | --- |
| Thickness | 1.1 | 1.05 |
| Knoop, hardness | 10.8 | 13.1 |
| MEK, MAR rubs | 60 | 20 |
| MEK, remove, rubs | 110 | 120 |

EXAMPLE X

Synthesis of 1,3,5-tri(1-chloro-1-methylethyl)benzene (TPTC)

90 grams of 1,3,5 triisopropenyl benzene (90% pure) was added to 300 ml of methylene chloride and cooled to 0°–5° C. HCl gas was bubbled into the solution through a glass sparger and after the HCl solution (3.2 equivalents) was complete, nitrogen gas was bubbled through the solution to remove any traces of HCl. Methylene chloride was removed, and the solid recrystallized from hexane. The yields of the trichloride were 86–99% before recrystallization and 68–76% after recrystallization.

The trichloride product is a white solid melting at 69°–71° C. Both $^{13}C$ and proton NMR confirmed the proton NMR showed a singlet at delta-7.6 corresponding to the aromatic hydrogens and a singlet at delta-2.0 for the methyl hydrogens.

EXAMPLE XI

TPTI From TPTC and Isocyanic Acid

To 60 ml of toluene containing 12.9 grams of isocyanic acid (300 m moles) was added 5 grams of TPTC (24.5 m moles). The solution was cooled to 0° C. using an ice bath, and 4 ml. of a 1 molar solution of $ZnCl_2$ in diethyl ether slowly added over 25 minutes. At the end of that time, volatiles were stripped off under vacuum (80°/25 mm Hg) and the crude residue analyzed by GLC (0.7% monoisocyanate diolefin; 11.9% diisocyanate mono-olefin; and 83% triisocyanate-TPTI). The triisocyanate was isolated by dissolving the crude mixture in hot hexane, filtered to remove small amounts of insolubles and cooled. Pure TPTI (m.p. 71°–72° C.) crystallized out on standing.

EXAMPLE XII

TPTI From TRIPEB (1,3,5-Tri-isopropenyl Benzene)

To 200 ml of toluene containing 40 grams of isocyanic acid (930 m moles) and 1 gram of dodecylbenzene sulfonic acid catalyst at 50° C. is added 20 grams (200 m moles) of TRIPEB over a period of one hour. Volatiles are stripped from the reaction mixture (~80°/25 mm Hg) and the residue taken up in hot hexane. On cooling 15 g of pure tri-iso-cyanate (TPTI) is isolated in a first crop.

EXAMPLE XIII

TPTU From TPTO (1,3,5-tri(1-hydroxy-1-methylethyl)Benzene

To 50.6 grams (200 m moles) of the triol (TPTO) is added 43 g (1 mole) of methyl carbamate, followed by the addition of 0.98 gram (10 m moles) of sulfuric acid. The mixture is heated at ~90° for 2 hours, cooled to room temperature and neutralized with aqueous sodium carbonate. Organics are extracted with methylene chloride, separated from the water layer, and dried over magnesium sulfate. Addition of hot hexane to the dried solution on standing yields 40 grams of TPTU, the desired tri-urethane.

EXAMPLE XIV

TPTU from TRIPEB(1,3,5-Triisopropenyl Benzene) and Methyl Carbamate

To 2.33 g (10 m moles) of 1,3,5-triisopropenyl benzene (85%) in 100 ml of methylene chloride solution was added 9.0 gram (209 m moles) of methyl carbamate and 0.19 gram of p-toluene sulfonic acid catalyst dissolve in 20 ml methylene chloride. After standing three days at room temperature, water (~20 ml) was added to the mixture and the methylene chloride layer separated and dried over magnesium sulfate. Addition of hot hexane to the dried solution gave on standing 1.1 g of the corresponding desired tri-urethane, m.p. 150°–151° C.

EXAMPLE XV

Cracking of TPTU To TPTI (Tri-Isocyanate)

To 2 g of TPTU is added 0.2 g of CaO and the mixture heated at 220°–240° (~20 mm Hg) for one hour. The solids are extracted with methylene chloride, filtered and hot hexane added. After standing, 1.2 grams of pure TPTI crystals separate; the tri-isocyanate melts at 71°–72° C.

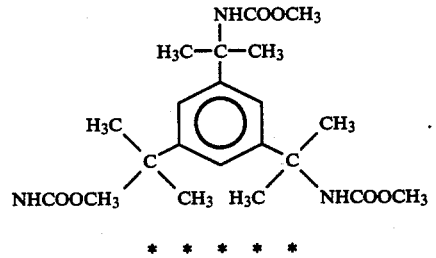

What is claimed is:

1. A compound of the formula: